(12) United States Patent
Wright et al.

(10) Patent No.: US 12,033,484 B2
(45) Date of Patent: *Jul. 9, 2024

(54) SYSTEMS AND METHODS FOR PREDICTIVE ENVIRONMENTAL FALL RISK IDENTIFICATION USING DYNAMIC INPUT

(71) Applicant: Electronic Caregiver, Inc., Las Cruces, NM (US)

(72) Inventors: Jacob R. Wright, Las Cruces, NM (US); Hannah S. Rich, Las Cruces, NM (US)

(73) Assignee: ELECTRONIC CAREGIVER, INC., Las Cruces, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/463,270

(22) Filed: Aug. 31, 2021

(65) Prior Publication Data

US 2021/0398410 A1 Dec. 23, 2021

Related U.S. Application Data

(63) Continuation of application No. 16/866,194, filed on May 4, 2020, now Pat. No. 11,113,943.

(Continued)

(51) Int. Cl.
*G08B 21/04* (2006.01)
*G06N 3/08* (2023.01)
*G06N 20/00* (2019.01)

(52) U.S. Cl.
CPC ........... *G08B 21/0423* (2013.01); *G06N 3/08* (2013.01); *G06N 20/00* (2019.01); *G08B 21/0438* (2013.01)

(58) Field of Classification Search
CPC ............ G08B 21/0423; G08B 21/0438; G06N 20/00; G06N 3/08

(Continued)

(56) References Cited

U.S. PATENT DOCUMENTS 5,211,642 A 5/1993 Clendenning
5,475,953 A 12/1995 Greenfield
(Continued)

FOREIGN PATENT DOCUMENTS

CA 2949449 A1 11/2015
CN 104361321 A 2/2015
(Continued)

OTHER PUBLICATIONS

"International Search Report" and "Written Opinion of the International Searching Authority," Patent Cooperation Treaty Application No. PCT/US2018/057814, Jan. 11, 2019, 9 pages.

(Continued)

*Primary Examiner* — Kerri L McNally
*Assistant Examiner* — Thang D Tran
(74) *Attorney, Agent, or Firm* — Carr & Ferrell LLP (57) ABSTRACT

In various exemplary embodiments the present technology is directed to methods and systems for predictive environmental fall risk identification for a user. A device may receive dynamic observations of an environmental map using a sensor. A device may determine the environmental map. A device may collect a set of risk factors for the environmental map using the sensor. A device may assess the set of risk factors for the environmental map for the user. A device may create a training set comprising the collected set of risk factors. A device may train an artificial neural network using the training set. A device may predict a fall risk of the user using the artificial neural network. A device may send an alert to the user based on the dynamic observations of the environmental map and the fall risk of the user.

20 Claims, 4 Drawing Sheets

Related U.S. Application Data (60) Provisional application No. 62/844,661, filed on May 7, 2019.

(58) Field of Classification Search
USPC ............................................. 340/573.1
See application file for complete search history.

(56) References Cited

U.S. PATENT DOCUMENTS

| | | | |
|---|---|---|---|
| 5,601,910 A * | 2/1997 | Murphy | D06N 7/0073 |
| | | | 442/84 |
| 6,665,647 B1 | 12/2003 | Haudenschild | |
| 7,233,872 B2 | 6/2007 | Shibasaki et al. | |
| 7,445,086 B1 * | 11/2008 | Sizemore | E06C 7/081 |
| | | | 182/108 |
| 7,612,681 B2 | 11/2009 | Azzaro et al. | |
| 7,971,141 B1 | 6/2011 | Quinn et al. | |
| 8,206,325 B1 | 6/2012 | Najafi et al. | |
| 8,771,206 B2 | 7/2014 | Gettelman et al. | |
| 9,317,916 B1 | 4/2016 | Hanina et al. | |
| 9,414,222 B1 * | 8/2016 | Dixon | G06Q 10/04 |
| 9,591,996 B2 | 3/2017 | Chang et al. | |
| 9,972,187 B1 | 5/2018 | Srinivasan et al. | |
| 10,387,963 B1 | 8/2019 | Leise et al. | |
| 10,628,635 B1 | 4/2020 | Carpenter, II et al. | |
| 10,692,011 B2 * | 6/2020 | Pathak | G06N 20/00 |
| 10,761,691 B2 | 9/2020 | Anzures et al. | |
| 10,813,572 B2 | 10/2020 | Dohrmann et al. | |
| 10,825,318 B1 * | 11/2020 | Williams | G08B 21/0484 |
| 11,113,943 B2 | 9/2021 | Wright et al. | |
| 11,213,224 B2 | 1/2022 | Dohrmann et al. | |
| 2002/0062342 A1 | 5/2002 | Sidles | |
| 2002/0196944 A1 | 12/2002 | Davis et al. | |
| 2004/0109470 A1 | 6/2004 | Derechin et al. | |
| 2005/0035862 A1 | 2/2005 | Wildman et al. | |
| 2005/0055942 A1 | 3/2005 | Maelzer et al. | |
| 2006/0001545 A1 * | 1/2006 | Wolf | G08B 21/0446 |
| | | | 340/686.1 |
| 2007/0238936 A1 | 10/2007 | Becker | |
| 2008/0010293 A1 | 1/2008 | Zpevak et al. | |
| 2008/0186189 A1 | 8/2008 | Azzaro et al. | |
| 2009/0094285 A1 | 4/2009 | Mackle et al. | |
| 2010/0124737 A1 | 5/2010 | Panzer | |
| 2011/0126207 A1 | 5/2011 | Wipfel et al. | |
| 2011/0145018 A1 | 6/2011 | Fotsch et al. | |
| 2011/0232708 A1 | 9/2011 | Kemp | |
| 2012/0025989 A1 | 2/2012 | Cuddihy et al. | |
| 2012/0075464 A1 | 3/2012 | Derenne et al. | |
| 2012/0120184 A1 | 5/2012 | Fornell et al. | |
| 2012/0121849 A1 | 5/2012 | Nojima | |
| 2012/0154582 A1 | 6/2012 | Johnson et al. | |
| 2012/0165618 A1 | 6/2012 | Algoo et al. | |
| 2012/0179067 A1 | 7/2012 | Wekell | |
| 2012/0179916 A1 | 7/2012 | Staker et al. | |
| 2012/0229634 A1 | 9/2012 | Laett et al. | |
| 2012/0253233 A1 * | 10/2012 | Greene | G16H 50/30 |
| | | | 600/592 |
| 2013/0000228 A1 * | 1/2013 | Ovaert | E04F 15/22 |
| | | | 428/179 |
| 2013/0127620 A1 | 5/2013 | Siebers et al. | |
| 2013/0145449 A1 | 6/2013 | Busser et al. | |
| 2013/0167025 A1 | 6/2013 | Patri et al. | |
| 2013/0204545 A1 | 8/2013 | Solinsky | |
| 2013/0212501 A1 | 8/2013 | Anderson et al. | |
| 2013/0237395 A1 | 9/2013 | Hjelt et al. | |
| 2013/0289449 A1 | 10/2013 | Stone et al. | |
| 2013/0303860 A1 | 11/2013 | Bender et al. | |
| 2014/0128691 A1 | 5/2014 | Olivier | |
| 2014/0148733 A1 | 5/2014 | Stone et al. | |
| 2014/0171039 A1 | 6/2014 | Bjontegard | |
| 2014/0171834 A1 | 6/2014 | DeGoede et al. | |
| 2014/0232600 A1 | 8/2014 | Larose et al. | |
| 2014/0243686 A1 | 8/2014 | Kimmel | |
| 2014/0257852 A1 | 9/2014 | Walker et al. | |
| 2014/0267582 A1 | 9/2014 | Beutter et al. | |
| 2014/0267625 A1 * | 9/2014 | Clark | G06T 7/70 |
| | | | 348/46 |
| 2014/0278605 A1 | 9/2014 | Borucki et al. | |
| 2014/0330172 A1 | 11/2014 | Jovanov et al. | |
| 2014/0337048 A1 | 11/2014 | Brown et al. | |
| 2014/0358828 A1 | 12/2014 | Phillipps et al. | |
| 2014/0368601 A1 | 12/2014 | deCharms | |
| 2015/0019250 A1 | 1/2015 | Goodman et al. | |
| 2015/0109442 A1 | 4/2015 | Derenne et al. | |
| 2015/0169835 A1 | 6/2015 | Hamdan et al. | |
| 2015/0359467 A1 | 12/2015 | Tran | |
| 2016/0026354 A1 * | 1/2016 | McIntosh | G06Q 10/06 |
| | | | 706/12 |
| 2016/0117470 A1 | 4/2016 | Welsh et al. | |
| 2016/0117484 A1 | 4/2016 | Hanina et al. | |
| 2016/0154977 A1 | 6/2016 | Jagadish et al. | |
| 2016/0217264 A1 | 7/2016 | Sanford | |
| 2016/0253890 A1 | 9/2016 | Rabinowitz et al. | |
| 2016/0267327 A1 | 9/2016 | Franz et al. | |
| 2016/0314255 A1 * | 10/2016 | Cook | G06F 16/906 |
| 2016/0379092 A1 * | 12/2016 | Kutliroff | G06T 7/73 |
| | | | 382/158 |
| 2017/0000387 A1 * | 1/2017 | Forth | G06N 7/01 |
| 2017/0000422 A1 | 1/2017 | Moturu et al. | |
| 2017/0024531 A1 | 1/2017 | Malaviya | |
| 2017/0055917 A1 | 3/2017 | Stone et al. | |
| 2017/0140631 A1 | 5/2017 | Pietrocola et al. | |
| 2017/0147154 A1 | 5/2017 | Steiner et al. | |
| 2017/0161614 A1 * | 6/2017 | Mehta | G06N 20/00 |
| 2017/0192950 A1 | 7/2017 | Gaither et al. | |
| 2017/0193163 A1 | 7/2017 | Melle et al. | |
| 2017/0197115 A1 | 7/2017 | Cook et al. | |
| 2017/0213145 A1 * | 7/2017 | Pathak | G06N 7/01 |
| 2017/0273601 A1 | 9/2017 | Wang et al. | |
| 2017/0337274 A1 | 11/2017 | Ly et al. | |
| 2017/0344706 A1 | 11/2017 | Torres et al. | |
| 2017/0344832 A1 * | 11/2017 | Leung | G08B 21/043 |
| 2018/0005448 A1 | 1/2018 | Choukroun et al. | |
| 2018/0075558 A1 | 3/2018 | Hill, Sr. et al. | |
| 2018/0129276 A1 * | 5/2018 | Nguyen | G06F 3/016 |
| 2018/0154514 A1 | 6/2018 | Angle et al. | |
| 2018/0165938 A1 * | 6/2018 | Honda | A61B 5/1113 |
| 2018/0182472 A1 * | 6/2018 | Preston | G16H 10/60 |
| 2018/0189756 A1 | 7/2018 | Purves et al. | |
| 2018/0233018 A1 * | 8/2018 | Burwinkel | A61B 5/1117 |
| 2018/0302403 A1 * | 10/2018 | Souders | H04L 63/0861 |
| 2018/0322045 A1 | 11/2018 | Sakui | |
| 2018/0322405 A1 | 11/2018 | Fadell et al. | |
| 2018/0342081 A1 * | 11/2018 | Kim | A61B 5/1117 |
| 2018/0360349 A9 | 12/2018 | Dohrmann et al. | |
| 2018/0368780 A1 * | 12/2018 | Bruno | A61B 5/1113 |
| 2019/0029900 A1 | 1/2019 | Walton et al. | |
| 2019/0042700 A1 | 2/2019 | Alotaibi | |
| 2019/0057320 A1 | 2/2019 | Docherty et al. | |
| 2019/0090786 A1 * | 3/2019 | Kim | G06N 3/08 |
| 2019/0116212 A1 | 4/2019 | Spinella-Mamo | |
| 2019/0130110 A1 | 5/2019 | Lee et al. | |
| 2019/0164015 A1 | 5/2019 | Jones, Jr. et al. | |
| 2019/0164261 A1 * | 5/2019 | Sunkavalli | G06N 3/045 |
| 2019/0196888 A1 | 6/2019 | Anderson et al. | |
| 2019/0197861 A1 * | 6/2019 | Tunnell | A61B 5/0205 |
| 2019/0220003 A1 * | 7/2019 | Sharma | G06N 7/01 |
| 2019/0220727 A1 | 7/2019 | Dohrmann et al. | |
| 2019/0259475 A1 | 8/2019 | Dohrmann et al. | |
| 2019/0282130 A1 | 9/2019 | Dohrmann et al. | |
| 2019/0286942 A1 | 9/2019 | Abhiram et al. | |
| 2019/0311792 A1 | 10/2019 | Dohrmann et al. | |
| 2019/0318165 A1 * | 10/2019 | Shah | G06N 20/00 |
| 2019/0385749 A1 | 12/2019 | Dohrmann et al. | |
| 2020/0012549 A1 * | 1/2020 | Johnsson | H04L 67/10 |
| 2020/0101969 A1 | 4/2020 | Natroshvili et al. | |
| 2020/0201648 A1 * | 6/2020 | Memon | G06F 9/54 |
| 2020/0219372 A1 * | 7/2020 | Kwatra | G06F 16/906 |
| 2020/0251220 A1 | 8/2020 | Chasko | |
| 2020/0327367 A1 * | 10/2020 | Ma | G06T 7/73 |
| 2020/0357256 A1 | 11/2020 | Wright et al. | |
| 2020/0357511 A1 | 11/2020 | Sanford | |
| 2021/0007631 A1 | 1/2021 | Dohrmann et al. | |

(56) References Cited

U.S. PATENT DOCUMENTS

| | | | |
|---|---|---|---|
| 2021/0273962 | A1 | 9/2021 | Dohrmann et al. |
| 2021/0358202 | A1 | 11/2021 | Tveito et al. |
| 2022/0022760 | A1 | 1/2022 | Salcido et al. |

FOREIGN PATENT DOCUMENTS

| | | | |
|---|---|---|---|
| CN | 106056035 A | 10/2016 | |
| CN | 107411515 A | 12/2017 | |
| CN | 111801645 A | 10/2020 | |
| CN | 111801939 A | 10/2020 | |
| CN | 111867467 A | 10/2020 | |
| CN | 113795808 | 12/2021 | |
| EP | 3740856 A1 | 11/2020 | |
| EP | 3756344 A1 | 12/2020 | |
| EP | 3768164 A1 | 1/2021 | |
| EP | 3773174 A1 | 2/2021 | |
| EP | 3815108 A1 | 5/2021 | |
| EP | 3920797 A1 | 12/2021 | |
| EP | 3944258 | 1/2022 | |
| IN | 202027033318 A | 10/2020 | |
| IN | 202027035634 A | 10/2020 | |
| JP | 2002304362 A | 10/2002 | |
| JP | 2005228305 A | 8/2005 | |
| JP | 2016525383 A | 8/2016 | |
| KR | 1020160040078 A | 4/2016 | |
| KR | 1020200105519 A | 9/2020 | |
| KR | 1020200121832 A | 10/2020 | |
| KR | 1020200130713 A | 11/2020 | |
| WO | WO2000005639 A2 | 2/2000 | |
| WO | WO2014043757 A1 | 3/2014 | |
| WO | WO2018032089 A1 | 2/2018 | |
| WO | WO2019143397 A1 | 7/2019 | |
| WO | WO2019164585 A1 | 8/2019 | |
| WO | WO2019182792 A1 | 9/2019 | |
| WO | WO2019199549 A1 | 10/2019 | |
| WO | WO2019245713 A1 | 12/2019 | |
| WO | WO2020163180 A1 | 8/2020 | |
| WO | WO2020227303 A1 | 11/2020 | |

OTHER PUBLICATIONS

"International Search Report" and "Written Opinion of the International Searching Authority," Patent Cooperation Treaty Application No. PCT/US2018/068210, Apr. 12, 2019, 9 pages.
"International Search Report" and "Written Opinion of the International Searching Authority," Patent Cooperation Treaty Application No. PCT/US2019/021678, May 24, 2019, 12 pages.
"International Search Report" and "Written Opinion of the International Searching Authority," Patent Cooperation Treaty Application No. PCT/US2019/025652, Jul. 18, 2019, 11 pages.
"International Search Report" and "Written Opinion of the International Searching Authority," Patent Cooperation Treaty Application No. PCT/US2019/034206, Aug. 1, 2019, 11 pages.
Rosen et al., "Slipping and Tripping: Fall Injuries in Adults Associated with Rugs and Carpets," Journal of Injury & Violence Research, 5(1), (2013), pp. 61-69.
Bajaj, Prateek, "Reinforcement Learning", GeeksForGeeks.org [online], [retrieved on Mar. 4, 2020], Retrieved from the Internet :<URL:https://www.geeksforgeeks.org/what-is-reinforcement-learning/>, 7 pages.
Kung-Hsiang, Huang (Steeve), "Introduction to Various RL Algorithms. Part I (Q-Learning, SARSA, DQN, DDPG)", Towards Data Science, [online], [retrieved on Mar. 4, 2020], Retrieved from the Internet :<URL:https://towardsdatascience.com/introduction-to-various-reinforcement-learning-algorithms-i-q-learning-sarsa-dqn-ddpg-72a5e0cb6287>, 5 pages.
Bellemare et al., A Distributional Perspective on Reinforcement Learning:, Proceedings of the 34th International Conference on Machine Learning, Sydney, Australia, Jul. 21, 2017, 19 pages.
Friston et al., "Reinforcement Learning or Active Inference?" Jul. 29, 2009, [online], [retrieved on Mar. 4, 2020], Retrieved from the Internet :<URL:https://doi.org/10.1371/journal.pone.0006421 PLoS ONE 4(7): e6421>, 13 pages.
Zhang et al., "DQ Scheduler: Deep Reinforcement Learning Based Controller Synchronization in Distributed SDN" ICC 2019—2019 IEEE International Conference on Communications (ICC), Shanghai, China, doi: 10.1109/ICC.2019.8761183, pp. 1-7.
"International Search Report" and "Written Opinion of the International Searching Authority," Patent Cooperation Treaty Application No. PCT/US2020/031486, Aug. 3, 2020, 7 pages.
"International Search Report" and "Written Opinion of the International Searching Authority," Patent Cooperation Treaty Application No. PCT/US2020/016248, May 11, 2020, 7 pages.
"Office Action", Australia Patent Application No. 2019240484, Nov. 13, 2020, 4 pages.
"Office Action", Australia Patent Application No. 2018403182, Feb. 5, 2021, 5 pages.
"Office Action", Australia Patent Application No. 2018409860, Feb. 10, 2021, 4 pages.
Leber, Jessica, "The Avatar Will See You Now", MIT Technology Review, Sep. 17, 2013, 4 pages.
"Office Action", India Patent Application No. 202027035634, Jun. 30, 2021, 10 pages.
"Office Action", India Patent Application No. 202027033121, Jul. 29, 2021, 7 pages.
"Office Action", Canada Patent Application No. 3088396, Aug. 6, 2021, 7 pages.
"Office Action", China Patent Application No. 201880089608.2, Aug. 3, 2021, 8 pages [17 pages with translation].
"Office Action", Japan Patent Application No. 2020-543924, Jul. 27, 2021, 3 pages [6 pages with translation].
"Office Action", Australia Patent Application No. 2019240484, Aug. 2, 2021, 3 pages.
"Office Action", Canada Patent Application No. 3089312, Aug. 19, 2021, 3 pages.
"Extended European Search Report", European Patent Application No. 18901139.8, Sep. 9, 2021, 6 pages.
"Office Action", Canada Patent Application No. 3091957, Sep. 14, 2021, 4 pages.
"Office Action", Japan Patent Application No. 2020-540382, Aug. 24, 2021, 7 pages [13 pages with translation].
"Extended European Search Report", European Patent Application No. 18907032.9, Oct. 15, 2021, 12 pages.
Marston et al., "The design of a purpose-built exergame for fall prediction and prevention for older people", European Review of Aging and Physical Activity 12:13, <URL:https://eurapa.biomedcentral.com/track/pdf/10.1186/s11556-015-0157-4.pdf>, Dec. 8, 2015, 12 pages.
Ejupi et al., "Kinect-Based Five-Times-Sit-to-Stand Test for Clinical and In-Home Assessment of Fall Risk in Older People", Gerontology (vol. 62), (May 28, 2015), <URL:https://www.karger.com/Article/PDF/381804>, May 28, 2015, 7 pages.
Festl et al., "iStoppFalls: A Tutorial Concept and prototype Contents", <URL:https://hcisiegen.de/wp-uploads/2014/05/isCtutorial.doku.pdf>, Mar. 30, 2013, 36 pages.
"Notice of Allowance", Australia Patent Application No. 2019240484, Oct. 27, 2021, 4 pages.
"Extended European Search Report", European Patent Application No. 19772545.0, Nov. 16, 2021, 8 pages.
"Office Action", India Patent Application No. 202027033318, Nov. 18, 2021, 6 pages.
"Office Action", Australia Patent Application No. 2018409860, Nov. 30, 2021, 4 pages.
"Office Action", Australia Patent Application No. 2018403182, Dec. 1, 2021, 3 pages.
"Office Action", Korea Patent Application No. 10-2020-7028606, Oct. 29, 2021, 7 pages [14 pages with translation].
"Office Action", Japan Patent Application No. 2020-543924, Nov. 24, 2021, 3 pages [6 pages with translation].
"Extended European Search Report", European Patent Application No. EP19785057, Dec. 6, 2021, 8 pages.
"Office Action", Australia Patent Application No. 2020218172, Dec. 21, 2021, 4 pages.
"Extended European Search Report", European Patent Application No. 21187314.6, Dec. 10, 2021, 10 pages.

(56) References Cited

OTHER PUBLICATIONS

"Notice of Allowance", Australia Patent Application No. 2018403182, Jan. 20, 2022, 4 pages.
"Office Action", Australla Patent Application No. 2018409860, Jan. 24, 2022, 5 pages.
"Office Action", China Patent Application No. 201880089608.2, Feb. 8, 2022, 6 pages.
"International Search Report" and "Written Opinion of the International Searching Authority," Patent Cooperation Treaty Application No. PCT/US2021/056060, Jan. 28, 2022, 8 pages.

* cited by examiner

SYSTEMS AND METHODS FOR PREDICTIVE ENVIRONMENTAL FALL RISK IDENTIFICATION USING DYNAMIC INPUT

CROSS-REFERENCE TO RELATED APPLICATIONS

The present continuation application claims the priority benefit of U.S. Non-Provisional patent application Ser. No. 16/866,194 filed on May 4, 2020 titled "Systems and Methods for Predictive Environmental Fall Risk Identification," which claims the priority benefit of U.S. Provisional Application Ser. No. 62/844,661 filed on May 7, 2019 titled "Systems and Methods for Predictive Environmental Fall Risk Identification," which are all hereby incorporated by reference in their entireties.

FIELD OF INVENTION

The present technology pertains to systems and methods for predictive environmental fall risk identification.

SUMMARY

In some embodiments the present disclosure is directed to a system of one or more computers which can be configured to perform particular operations or actions by virtue of having software, firmware, hardware, or a combination thereof installed on the system that in operation causes or cause the system to perform actions and/or method steps as described herein.

In various embodiments the present technology is methods for predictive environmental fall risk identification for a user. In some embodiments the method comprises: (a) receiving dynamic observations of an environmental map using a sensor; (b) determining the environmental map; (c) collecting a set of risk factors for the environmental map using the sensor; (d) assessing the set of risk factors for the environmental map for the user; (e) creating a first training set comprising the collected set of risk factors; (f) training an artificial neural network in a first stage using the first training set; (g) creating a second training set for a second stage of training comprising the first training set and the dynamic observations of the environmental map; (h) training the artificial neural network in the second stage using the second training set; (i) predicting a fall risk of the user using the artificial neural network; and (j) sending an alert to the user based on the dynamic observations of the environmental map and the fall risk of the user.

In various exemplary embodiments the sensor includes but is not limited to a visual sensor. In some embodiments the sensor includes a Radio Frequency (RF) sensor, light detection and ranging sensor ("LiDAR"), an audio sensor, a temperature sensor, a light sensor, and the like.

BRIEF DESCRIPTION OF THE DRAWINGS

Certain embodiments of the present technology are illustrated by the accompanying figures. It will be understood that the figures are not necessarily to scale. It will be understood that the technology is not necessarily limited to the particular embodiments illustrated herein.

DETAILED DESCRIPTION

The detailed embodiments of the present technology are disclosed here. It should be understood, that the disclosed embodiments are merely exemplary of the invention, which may be embodied in multiple forms. Those details disclosed herein are not to be interpreted in any form as limiting, but as the basis for the claims.

To prevent falls, home-health care systems combine services like emergency alerts, with an initial fall hazard assessment of the home by a hired person. Some potential hazards are not pre-defined and pre-existing. Therefore, visual inspection for comparison to common safety standards, as an identification technique, cannot quantitatively predict risks not specifically standardized. The integration of health data standardization into Machine Learning (ML) is necessary for an accurate method of detecting hazards, which improves risk identification as it detects hazards. Embodiments of the present technology have not been previously been pursued for various reasons including because data sets were not available to train ML models to recognize risks. Additionally, the infrastructure to deploy the present technology, as well as an infrastructure to gather the training data, was either absent or unavailable. ML and deep learning are newly utilized tools in camera technology that are applied to embodiments of the present technology.

Various embodiments of the present technology use ML in the context of camera technology and home-health as a solution to increase safety in the home environment. For example, the type of ML that uses Reinforced Learning (RL) to produce the Environmental Fall Risks (EFR™) associated, which is dependent upon the individual (i.e., a user) and (changes in) time and notifies at-risk individuals.

Some embodiments of the present technology are a solution that reduces the high cost of home-health-care monitoring while decreasing hazards and preventing falls, and maintaining a user's safety and independence. Embodiments of the present technology are environment assessment systems and methods that identify risks that human interpretation is unable to anticipate, notice risks quickly, and alert the user. Embodiments of the present technology include a simulated environment that incorporates near-real-time technology to predict and detect risks.

Some embodiments of the present technology use simulations and visual sensors to produce Reinforced Learning (RL) models that accurately predict potential and existing EFR™, as well as identify newly developed EFR™ in near-real time. Potential and existing factors include furniture placement, room-dependent risk, user's individual fall risk, and the progression of time. Each room in an environment has a calculated EFR™ from contributing factors. Exemplary contributing factors include floor changes (e.g. traveling from rug to carpet, tile to rug, etc.), uneven floors (i.e. uneven tiles), room-dependent baseline (bathrooms have high fall risk), and furniture placement. Additional exemplary contributing factors of environmental fall risks are not physical textures/obstructions and include causalities of non-physical attributes (i.e. temperature, light conditions, ambient audio levels, and the like) Changes in the environment lead to newly developed risks (e.g. as a puddle of water forming). Time progression calculates in near-real time changing EFR™ for room-dependent risk and individual fall risk factors combined.

According to various embodiments of the present technology, to assess furniture placement and room-dependent risks, predefined factors and initial risk values improve as the model performs additional sequences. For example, risk values for suggested furniture rearrangement may be defined as potential and existing risks, which are high (low) if an initial value is greater than or equal to sixty percent (less than thirty percent), becomes high (low) for greater than fifty percent (less than ten percent) after a sequence.

Figure 2:
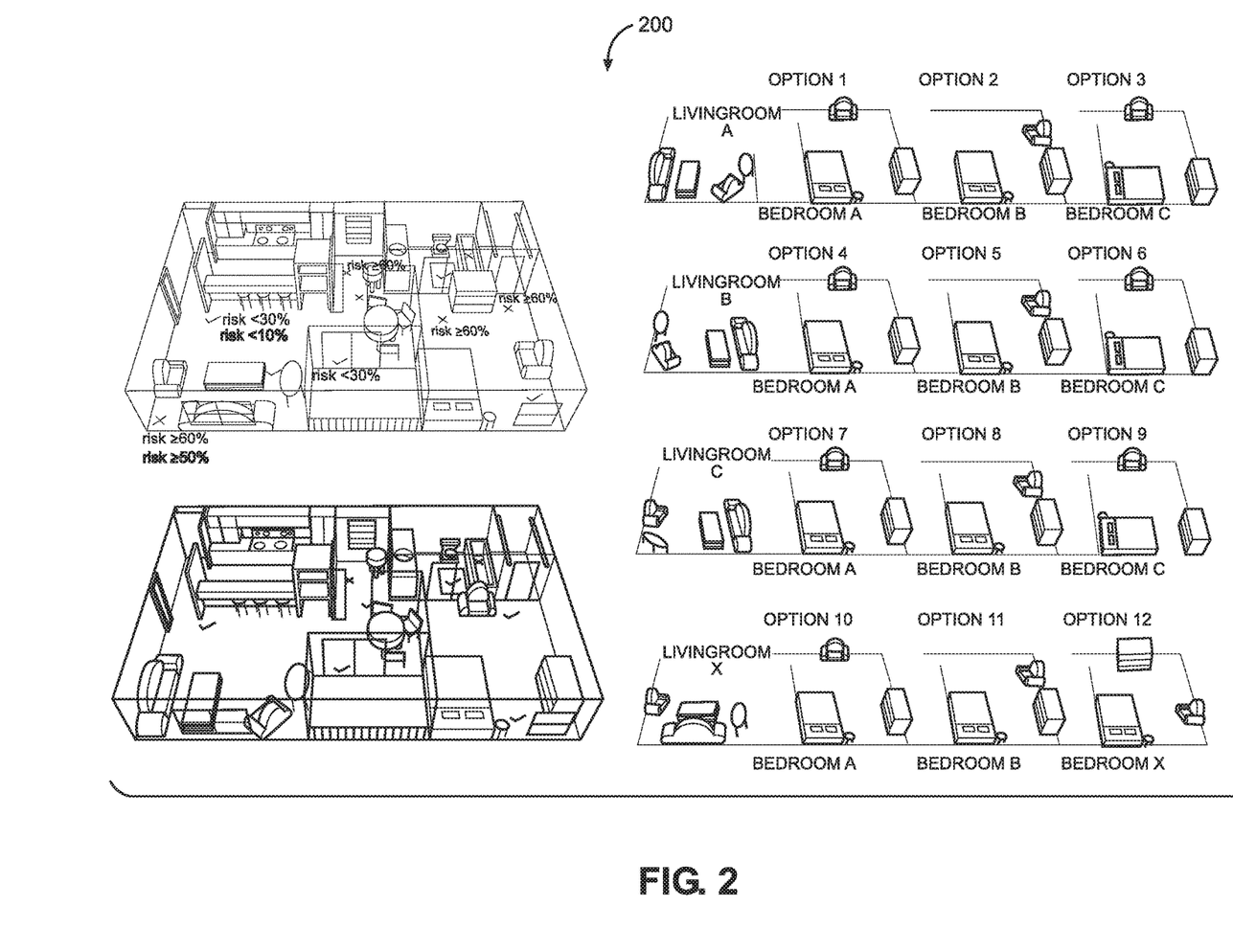
FIG. 2 illustrates an environmental map for predictive environmental fall risk identification according to exemplary embodiments of the present technology.

In various embodiments of the present technology, these models are produced with training data gathered and analyzed by systems of the present technology to include all factors listed changing in time and output new fall risks. For the change in time, the RL model of the user and the EFR™ is integrated with visual sensors. For example, a person with 75 percent individual fall risk is in a room with 0 percent, their total does not change. Now, the same person in a room with 21.3 percent risk, then the total risk is increased. There is also a dependent relationship on time. The longer the person is in a room, the higher the risk (i.e., total risk includes individual, room, and time). For example, this baseline may be established for an equation that depends on time (see equation 1 below):

$$\text{Fall risk} = f(t) = 0.75t + 0.213 \cdot t^2 \quad \text{(Equation 1)},$$

where 0.213 represents the room's baseline progressing in time and 0.75 t represents the person's individual risk in time. The factor 0.213—Bedroom fall risk is from fall analysis associated with rugs or carpets. See Rosen, et. al. in US National Library of Medicine (2013), refer to FIG. 2 footnotes. By including more variables, the technique presented here improves the room-specific values as it becomes better defined. Equation 1 is an exemplary equation and in various embodiments the equation is linear, logarithmic, etc. Similarly for the risk unit scores that determine visual sensor placement, these values were used for illustrative purposes and will vary from environment-to-environment and improve in accuracy as data is collected through time using ML.

In some embodiments of the present technology, for newly detected risks (puddle forming), the same visual sensors that detected the time someone remained in a room have also been placed to maximize square-feet covered. If the shower has 1 major risk, it has a score of fifty risk units. If the living room area with a view of the kitchen has several medium and minor risks with a score of two-hundred risk units, a sensor is placed there instead of in the bathroom.

Embodiments of the present technology use a trained model to automatically identify hazards and notify at-risk individuals of RL-identified falling hazards and EFR™. Using depth cameras and on-board neural network processing, this RL technique; identifies common and ambiguous Environmental Fall Risks (EFR) in real time, incorporates individual variables, and reduce health costs by preventing falls.

Figure 1:
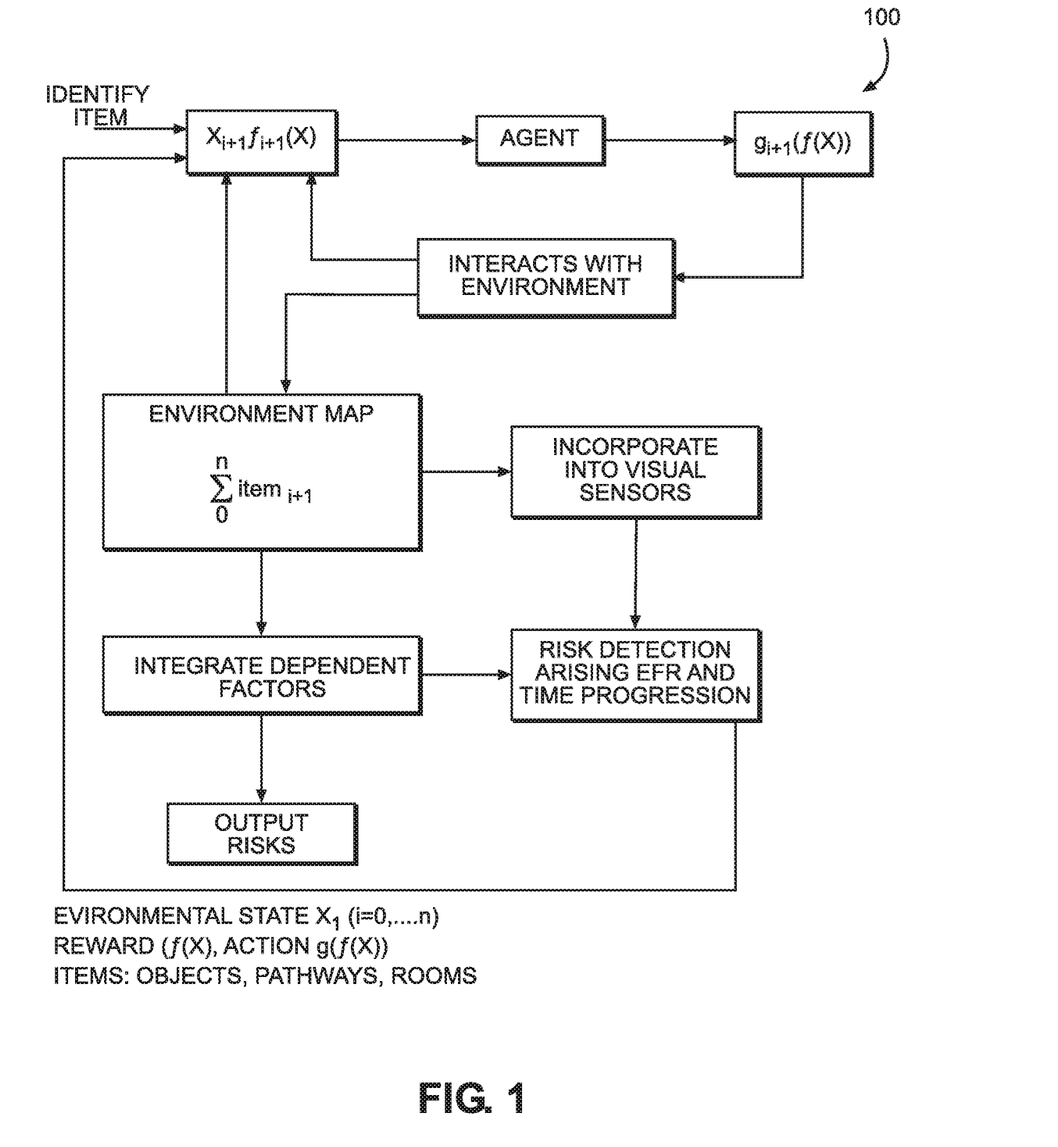
FIG. 1 is a flow chart of methods for predictive environmental fall risk identification according to exemplary embodiments of the present technology.

FIG. 1 is a flow chart 100 of methods for predictive environmental fall risk identification according to exemplary embodiments of the present technology. FIG. 1 shows a simulation process implemented to predict and identify Environmental Fall Risks (EFR™). The first step in the simulation process is input information that is taken by an agent using Reinforced Learning (RL) from measurements of environment state, with objects, to start mapping the environment in three dimensions. Methods and systems of the present technology take an action based off what is detected by interacting with the surroundings. The agent evaluates actions through a reward function and learns how to improve capabilities. For example, the reward function stipulates that all goals can be achieved by maximizing the expected future reward over all sequences. If the agent takes a good action, the agent gets a positive reward, which makes the agent want to maximize accumulative reward and achieve highest possible reward, (i.e. over all sequences, the expected future reward is maximized). For example, the measurement and action taken in sequence i=1 has rank 10, good=10, and the agent can achieve rank 10+i for each sequence completed. Additionally, the more completed sequences, the faster systems and methods of the present technology improve with less interaction.

In various embodiments the agent is a self-driving car that creates an environmental map (e.g., a map of a home). For example, small computers connected to sensors with ML models deployed to them assess and identify fall risks. The agent (e.g., a self-driving car) produces a baseline of the environment and environment optimization recommendations (e.g., rearranging furniture, lighting adjustments, etc.), as well as the baseline of the RL that the sensors use to detect changes.

FIG. 2 illustrates an environmental map 200 for predictive environmental fall risk identification according to exemplary embodiments of the present technology. FIG. 2 shows fall risks are established by incorporating items in the Environmental Map with users' individual risk, progression in time, and predefined dependent factors. Contributing factors include furniture placement, floor changes (risks increase when traveling from a carpet to tile, rug to carpet or tile, etc.), and room-dependent risks. Variables for room-dependent risk for falls include 35.7% in the bathroom, 21.3% in the bedroom, and 15.3% in the kitchen. The percentages are provided as examples and are non-limiting.

According to various exemplary embodiments the agent starts the initial sequence on the left by the front door, goes into the bedroom, and finishes the last sequence after going through the kitchen. As the agent composes the map and assesses corresponding risks, both become better defined with each sequence. For example, at the starting point by the front door, initial sequence $x_{i+1} = x_{0+1} = x_1$ with $f_1(x)$ and $g_1(f(x))$ for input of the state. At the next sequential point (i=1) the agent has interacted, detected what should be included in the next environmental state $x_2$, mapped them, and identified associated risks. This equation is provided as an example and its accuracy improves using ML as additional data is collected. For example, in general, by increasing solidity as the agent establishes the model, for low-to-no risk by check marks (✓), and for medium-to-high risks by cross marks (X). The light and dark percentages represent unfinished and finished models of risk, respectively. Once the bedroom is reached, as depicted here, the EFR™ assessment from the front door through the living room is finished. At this point, the model has improved its evaluation of high-risks to have a baseline of 50% instead of 60% for those areas. The initial 60% is from different room factors, e.g. 21.3% for the bedroom, combined with user's individual fall risk. This decrease to 50% is from evaluating furniture placement and factoring that in. Risks from the sliding glass door through hallway to kitchen (where it ends) are still unfinished here because additional directions through path-ways have yet to be considered (but will be when it ends). The equation is provided as an example and is non-limiting.

In various exemplary embodiments of the present technology the agent needs to figure out the map and identify if the agent is in a bedroom or bathroom, and so on, while simultaneously identifying and mapping risks (e.g. from furniture or rug placement). An individual user is notified of specific risks and furniture rearrangement(s) is suggested with associated changes in risks. For example, bedroom is high-risk from the room itself (21.3%) and dresser position (35%), combining (0.213+035=0.563) for total baseline risk of over fifty percent (56.3%). If the chair and couch are switched, this decreases to 21.3%. Also, one should be careful walking into the kitchen from the hall, the change of tile yields a high-risk for falls. Last, the agent includes user's individual fall risk and time progression. For example, say a user with a constant fall risk of seventy-five percent (75%) walks into the bedroom (21.3%), their risk, f(t), is now f(t) 0.75+0.213*t, the factor of time scales differently for different rooms. See Rosen, T., Mack, K. A., & Noonan, R. K. (2013), "Slipping and tripping: fall injuries in adults associated with rugs and carpets," *Journal of injury &violence research,* 5(1), 61-69. doi:10.5249/jivr.v5i1.177. In various embodiments, all these factors are included in EFR™ assessment and integrated into the visual sensors to be able to detect newly developed risks in near-real-time.

Results for different furniture arrangements will output options in terms of priority based off the corresponding change in EFR percentages. Those risks are based on a room by room basis combined into overall improvement. From the method explained in FIG. 1, for incorporating dependent factors, visual sensors, and time progression, the output risks could be determined from a number of numerical methods. For illustrative purposes here, linear regression will be used as an example of one method. Linear regression, where the regression model fits multiple lines (of the form y=mx+b) to data points to find the best fit, could be implemented in three-dimensional space here by Principle Component Analysis (PCA), which minimizes the average distance squared from a point to that (best fit) line, followed by anomaly ranking method like isolation forests. The method consists of adapting the method for one dimensional data to three dimensional. The regression line/predicted response value for $i^{th}$ observation, is $h(x_i)=\beta_0+\beta_1 x_i$ where $\beta_0$ and $\beta_1$ are regression coefficients and represent y-intercept and slope of the regression line, respectively. Then using least squares: $y_i=\beta_0+\beta_1 x_1+\varepsilon_i = h(x_i)+\varepsilon_i \rightarrow \varepsilon_i=u_i-h(x_i)$.

Using PCA to span this in the form $r=r(x_i, y_i, z_i)$, for outputting the normal vector for a two-dimensional plane, or direction vector for a line, and a point on that plane or line in three-dimension space. In other words, finds $\beta_0$ and $\beta_1$ to minimize the average distance squared from a point to that line, h(x), and that vector is used as path length, h(x), in the Isolation Forest algorithm. It is an anomaly detection method that provides a rank, or score s(x, n), reflecting the degree of anomaly(s).

$$s(x,n)=2^{-E(h(x))/c(n)}; \quad c(n)=2H(n-1)-(2(n-1)/n)$$

$$E(h(x)) \rightarrow c(n); \quad s(x,n) \rightarrow 0.5$$

$$E(h(x)) \rightarrow 0; \quad s(x,n) \rightarrow 1$$

$$E(h(x)) \rightarrow n-1; \quad s(x,n) \rightarrow 0$$

Where h(x)—Path length, c(n)—Measure of convergence, s(x,n)—Anomaly score of an instance x, H(i)—Harmonic number, estimated by ln(i)+0.5772156649, and E(h(x))—Average of h(x) averaged over a forest of random trees. The algorithm would use individual room factors as the coefficients for the linear regression, from before, f(t) =0.75+0.213*t (the example of a person with 75% individual fall risk being in the bedroom with its 21.3% risk).

Many different numerical methods can be employed to accomplish the results of this invention, one component of which is to yield multiple options for different furniture arrangements that are safer in terms of EFRs. For example, the individual rooms have rearrangements that decrease the EFR (Table 1) for those rooms individually and are contributing factors to the options outputted for the whole environment. This can be seen in the following table, Table 2, and FIG. 2, where the rank is reflected in the option numbers starting from "1" as the highest rank (i.e. most preferable). It is worth noting that only the bedroom and livingroom are considered here, and that this is for clarity (the other areas of the environment not included will be, as necessary, for the invention).

TABLE 1

Individual Room Rearrangements & Factors

| Room | Change in EFR | Room | Change in EFR |
|---|---|---|---|
| Livingroom A | 50% | Bedroom A | 60% |
| Livingroom B | 35% | Bedroom B | 50% |
| Livingroom C | 15% | Bedroom C | 40% |
| Livingroom X | 0% | Bedroom X | 0% |

TABLE 2

House Rearrangement Options

| Option No. | Room Combination | Change in EFR |
|---|---|---|
| 1 | Livingroom A, Bedroom A | 55% |
| 2 | Livingroom A, Bedroom B | 50% |
| 3 | Livingroom A, Bedroom C | 45% |
| 4 | Livingroom B, Bedroom A | 47.5% |
| 5 | Livingroom B, Bedroom B | 42.5% |
| 6 | Livingroom B, Bedroom C | 37.5% |
| 7 | Livingroom C, Bedroom A | 37.5% |
| 8 | Livingroom C, Bedroom B | 32.5% |
| 9 | Livingroom C, Bedroom C | 27.5% |
| 10 | Livingroom X, Bedroom A | 27.5% |
| 11 | Livingroom X, Bedroom B | 25% |
| 12 | Livingroom X, Bedroom X | 0% |

The combinations with their respective risks in the table are presented by percentages, here all positive percentages represented a decrease in EFR. Notice in option 1, depicted on the bottom-left in FIG. 2 and in FIG. 3, how this combination decreases the EFR by fifty-five percent. The rearrangement illustrated here is the optimal change from the original layout, depicted on the top-left in FIG. 2, representing Livingroom X and Bedroom X. Consider option 10, which has no change to the Livingroom and uses Bedroom A. This yields a sixty percent (60%) decrease in bedroom EFR and a total decrease overall of about twenty-eight percent (28%). The changes to the furniture arrangement in the bedroom are more important because it has a higher EFR on its own, of about 21.3% total as previously mentioned (Rosen, T., et. Al, 2013). This is reflected again when comparing options 3 and 4, the higher-risk areas are ranked appropriately in the evaluation and output of furniture rearrangement.

Figure 3:
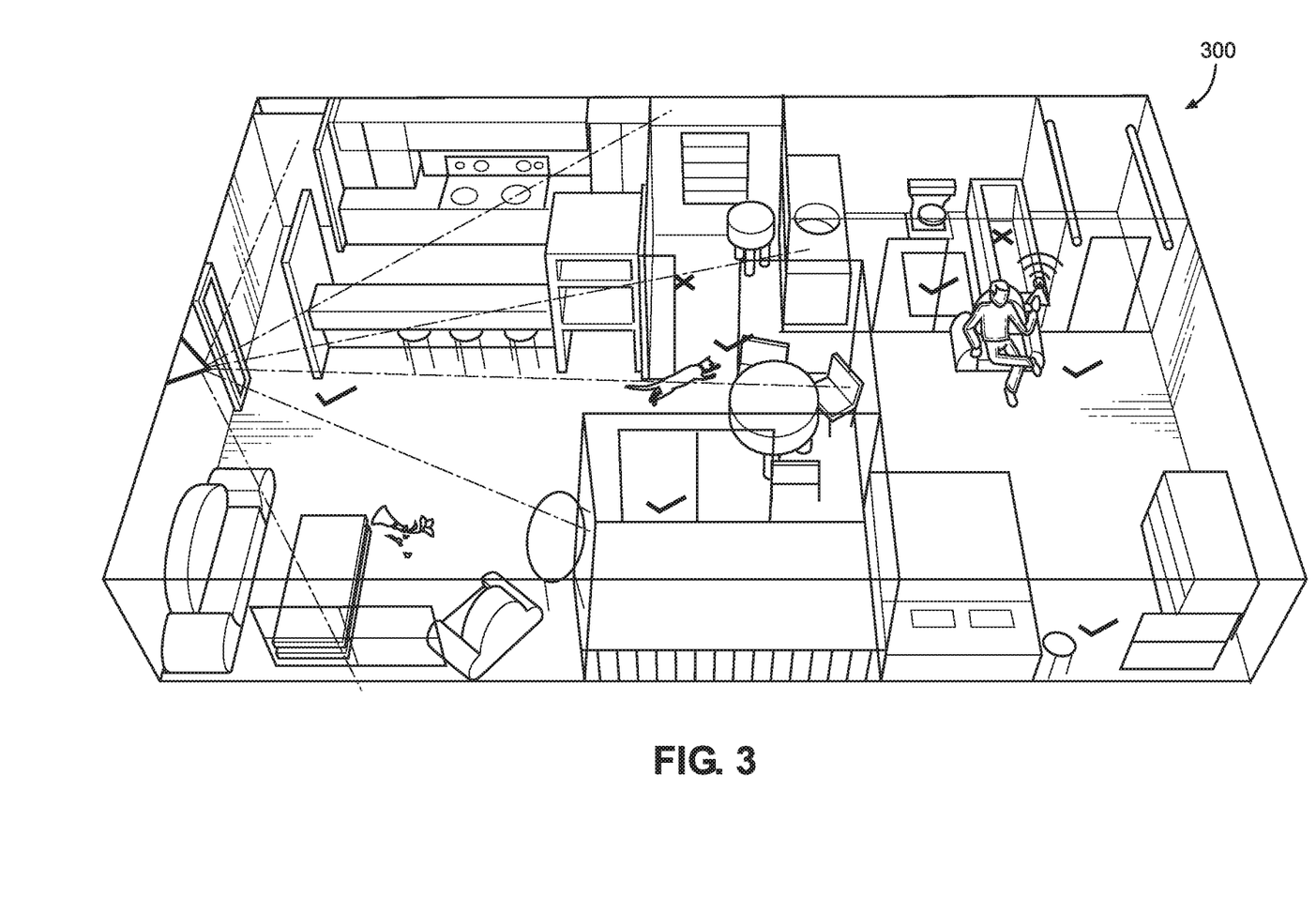
FIG. 3 illustrates an environmental map for predictive environmental fall risk identification with changes in the environment being detected according to exemplary embodiments of the present technology.

FIG. 3 illustrates an environmental map 300 for predictive environmental fall risk identification with changes in the environment being detected according to exemplary embodiments of the present technology. FIG. 3 shows new risks associated with furniture rearrangement, how changes in the environment are detected by the visual sensors using RL to identify newly developed risks, and placement of visual sensors to maximize sq.-ft coverage. Maximized coverage gives the ability to identify and detect both, newly formed risks, and time remained in the room (or absence thereof). For example, FIG. 3 shows a cat has knocked over a vase, forming a puddle changing the fall risk for a user. In near-real-time, the user is notified of the change in fall risk.

Figure 4:
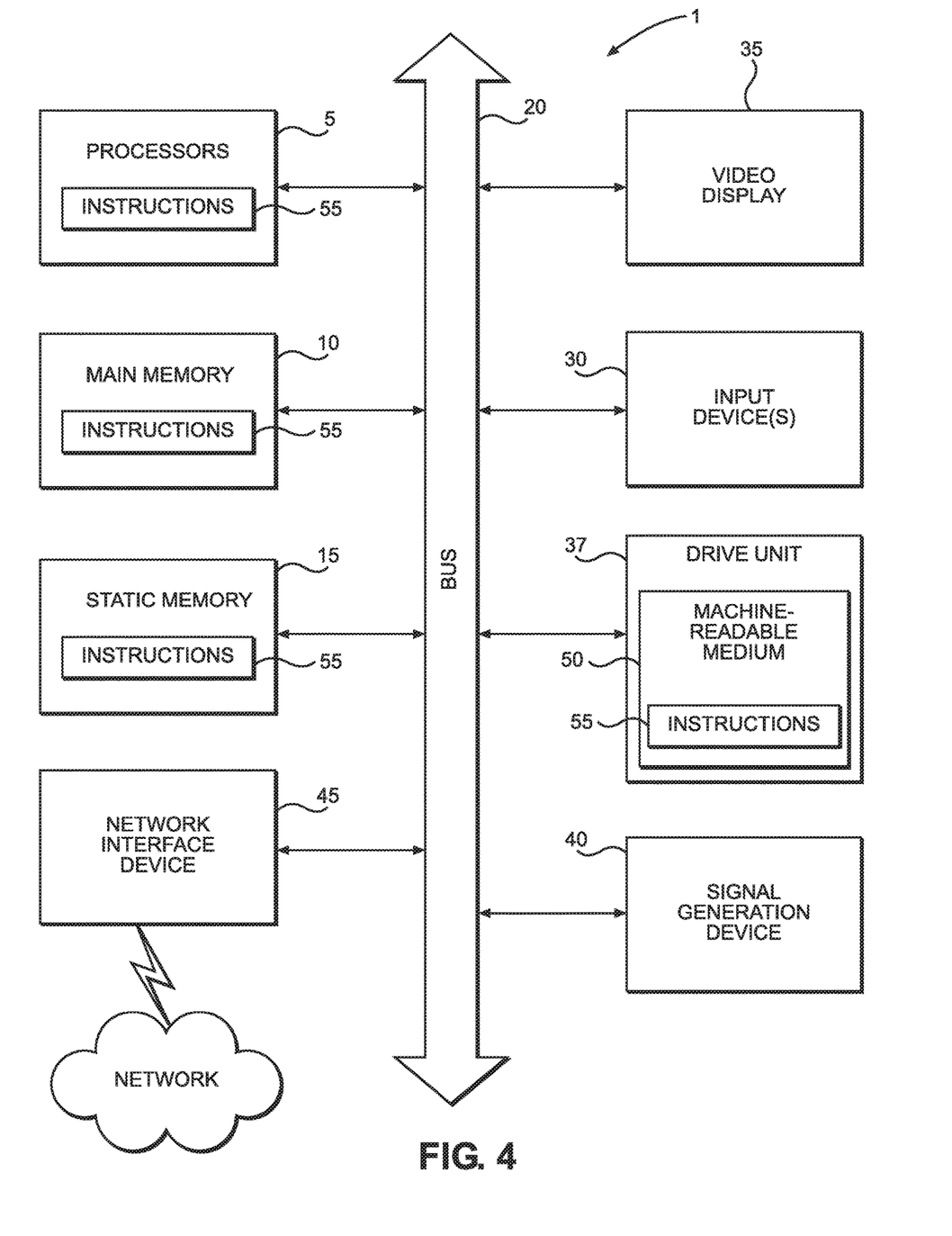
FIG. 4 illustrates a computer system according to exemplary embodiments of the present technology.

FIG. 4 illustrates a computer system according to exemplary embodiments of the present technology. FIG. 4 is a diagrammatic representation of an example machine in the form of a computer system 1, within which a set of instructions for causing the machine to perform any one or more of the methodologies discussed herein may be executed. In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a personal computer (PC), a tablet PC, a set-top box (STB), a personal digital assistant (PDA), a cellular telephone, a portable music player (e.g., a portable hard drive audio device such as an Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1 includes a processor or multiple processor(s) 5 (e.g., a central processing unit (CPU), a graphics processing unit (GPU), or both), and a main memory 10 and static memory 15, which communicate with each other via a bus 20. The computer system 1 may further include a video display 35 (e.g., a liquid crystal display (LCD)). The computer system 1 may also include an alpha-numeric input device(s) 30 (e.g., a keyboard), a cursor control device (e.g., a mouse), a voice recognition or biometric verification unit (not shown), a drive unit 37 (also referred to as disk drive unit), a signal generation device 40 (e.g., a speaker), and a network interface device 45. The computer system 1 may further include a data encryption module (not shown) to encrypt data.

The disk drive unit 37 includes a computer or machine-readable medium 50 on which is stored one or more sets of instructions and data structures (e.g., instructions 55) embodying or utilizing any one or more of the methodologies or functions described herein. The instructions 55 may also reside, completely or at least partially, within the main memory 10 and/or within the processor(s) 5 during execution thereof by the computer system 1. The main memory 10 and the processor(s) 5 may also constitute machine-readable media.

The instructions 55 may further be transmitted or received over a network via the network interface device 45 utilizing any one of a number of well-known transfer protocols (e.g., Hyper Text Transfer Protocol (HTTP)). While the machine-readable medium 50 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

One skilled in the art will recognize that the Internet service may be configured to provide Internet access to one or more computing devices that are coupled to the Internet service, and that the computing devices may include one or more processors, buses, memory devices, display devices, input/output devices, and the like. Furthermore, those skilled in the art may appreciate that the Internet service may be coupled to one or more databases, repositories, servers, and the like, which may be utilized in order to implement any of the embodiments of the disclosure as described herein.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

In the description, for purposes of explanation and not limitation, specific details are set forth, such as particular embodiments, procedures, techniques, etc. in order to provide a thorough understanding of the present technology. However, it will be apparent to one skilled in the art that the present technology may be practiced in other embodiments that depart from these specific details.

While specific embodiments of, and examples for, the system are described above for illustrative purposes, various equivalent modifications are possible within the scope of the system, as those skilled in the relevant art will recognize. For example, while processes or steps are presented in a given order, alternative embodiments may perform routines having steps in a different order, and some processes or steps may be deleted, moved, added, subdivided, combined, and/or modified to provide alternative or sub-combinations. Each of these processes or steps may be implemented in a variety of different ways. Also, while processes or steps are at times shown as being performed in series, these processes or steps may instead be performed in parallel, or may be performed at different times.

While various embodiments have been described above, it should be understood that they have been presented by way of example only, and not limitation. The descriptions are not intended to limit the scope of the present technology to the particular forms set forth herein. To the contrary, the present descriptions are intended to cover such alternatives, modifications, and equivalents as may be included within the spirit and scope of the present technology as appreciated by one of ordinary skill in the art. Thus, the breadth and scope of a preferred embodiment should not be limited by any of the above-described exemplary embodiments.

What is claimed is:

1. A method for predictive environmental fall risk identification for a user, the method comprising:
    receiving dynamic observations of an environmental map using a sensor;
    determining the environmental map;
    collecting a set of risk factors for the environmental map using the sensor;
    assessing the set of risk factors for the environmental map for the user;
    creating a training set comprising the collected set of risk factors for the environmental map;
    training an artificial neural network using the training set comprising the collected set of risk factors for the environmental map and the dynamic observations of the environmental map;
    predicting a fall risk of the user using the artificial neural network, the fall risk based on the user, room and time in the room by the user; and
    sending an alert to the user based on the dynamic observations of the environmental map and the fall risk of the user and suggesting a furniture rearrangement in the room to reduce the fall risk.

2. The method recited in claim 1, further comprising:
    identifying commonly occurring hazards that may cause a fall including one or more of poor lighting in a stairwell and water spills on tile floors.

3. The method recited in claim 1, further comprising:
    optimizing placement of the sensor, the optimizing of the placement of the sensor including maximizing coverage to identify and detect both newly formed risks and the time remained in the room by the user.

4. The method recited in claim 1, wherein the assessing the set of risk factors for the environmental map for the user comprises risks associated with different rooms in the environmental map, the risks associated with the different rooms in the environmental map being better defined using machine-learning to yield predictive identifiers.

5. The method recited in claim 1, wherein the sensor is a visual sensor.

6. The method recited in claim 1, wherein the sensor is a radio frequency sensor.

7. The method recited in claim 1, wherein the sensor is an audio sensor.

8. The method recited in claim 1, wherein the sensor is a light detection and ranging sensor.

9. The method recited in claim 1, wherein the fall risk of the user increases when the user travels from a carpet floor to a tile floor.

10. The method recited in claim 1, wherein the fall risk of the user increases when the user travels from a rug floor to a carpet floor.

11. A system for predictive environmental fall risk identification for a user, the system comprising:
    a sensor, the sensor providing dynamic observations of an environmental map;
    at least one processor; and
    a memory storing processor-executable instructions, wherein the at least one processor is configured to implement the following operations upon executing the processor-executable instructions:
    determining the environmental map;
    collecting a set of risk factors for the environmental map using the sensor;
    assessing the set of risk factors for the environmental map for the user;
    creating a training set comprising the collected set of risk factors for the environmental map;
    training an artificial neural network using the training set comprising the collected set of risk factors for the environmental map and the dynamic observations of the environmental map;
    predicting a fall risk of the user using the artificial neural network, the fall risk based on the user, room and time in the room by the user; and
    sending an alert to the user based on the dynamic observations of the environmental map and the fall risk of the user and suggesting a furniture rearrangement in the room to reduce the fall risk.

12. The system of claim 11, further comprising the processor-executable instructions including identifying commonly occurring hazards that may cause a fall including one or more of poor lighting in a stairwell and water spills on tile floors.

13. The system of claim 11, further comprising the processor-executable instructions including optimizing placement of the sensor, the optimizing of the placement of the sensor including maximizing coverage to identify and detect both newly formed risks and the time remained in a room by the user.

14. The system of claim 11, further comprising the processor-executable instructions including wherein the assessing the set of risk factors for the environmental map for the user comprises risks associated with different rooms in the environmental map, the risks associated with the different rooms in the environmental map being better defined using machine-learning to yield predictive identifiers.

15. The system of claim 11, wherein the sensor is a visual sensor.

16. The system of claim 11, wherein the sensor is a radio frequency sensor.

17. The system of claim 11, wherein the sensor is an audio sensor.

18. The system of claim 11, wherein the sensor is a light detection and ranging sensor.

19. The system of claim 11, wherein the fall risk of the user increases when the user travels from a carpet floor to a tile floor.

20. The system of claim 11, wherein the fall risk of the user increases when the user travels from a rug floor to a carpet floor.

* * * * *